US009192342B2

(12) United States Patent
Roudergues et al.

(10) Patent No.: US 9,192,342 B2
(45) Date of Patent: Nov. 24, 2015

(54) PATIENT HEAD SUPPORT APPARATUS FOR IMAGING

(75) Inventors: David Roudergues, Courbevoie (FR); Yann Lecuyer, Paris (FR); Philippe Congy, Meaux (FR)

(73) Assignee: Carestream Health, Inc., Rochester, NY (US)

( * ) Notice: Subject to any disclaimer, the term of this patent is extended or adjusted under 35 U.S.C. 154(b) by 77 days.

(21) Appl. No.: 14/113,441

(22) PCT Filed: Jun. 9, 2011

(86) PCT No.: PCT/IB2011/002037
§ 371 (c)(1),
(2), (4) Date: Oct. 23, 2013

(87) PCT Pub. No.: WO2012/168756
PCT Pub. Date: Dec. 13, 2012

(65) Prior Publication Data
US 2014/0079182 A1  Mar. 20, 2014

(51) Int. Cl.
*A61B 6/04* (2006.01)
*A61B 6/00* (2006.01)
*A61B 6/03* (2006.01)

(52) U.S. Cl.
CPC . *A61B 6/04* (2013.01); *A61B 6/032* (2013.01); *A61B 6/0421* (2013.01); *A61B 6/501* (2013.01)

(58) Field of Classification Search
CPC ................ A61B 6/0421; A61B 6/501
See application file for complete search history.

(56) References Cited

U.S. PATENT DOCUMENTS

| | | | |
|---|---|---|---|
| 2,903,588 A * | 9/1959 | Minnich | 378/180 |
| 3,737,660 A | 6/1973 | Ando et al. | |
| 3,875,412 A | 4/1975 | Hozumi | |
| 5,263,494 A | 11/1993 | Margelos et al. | |
| 5,642,392 A | 6/1997 | Nakano et al. | |
| 2007/0269001 A1 * | 11/2007 | Maschke | 378/38 |

FOREIGN PATENT DOCUMENTS

EP  0534548  3/1993

OTHER PUBLICATIONS

International Search Report completed Mar. 20, 2012 for International Application No. PCT/IB2011/002037, 2 Pages.

* cited by examiner

*Primary Examiner* — Hoon Song

(57) ABSTRACT

A support apparatus for positioning a patient's head in an imaging apparatus. A main body has opposing first and second sides and supports first and second holding members for positioning against the patient's head. The first holding member has a first reference position along the first side of the main body and is coupled to a first transport apparatus that extends outward from the main body. The second holding member has a second reference position along the second side of the main body and is coupled to a second transport apparatus that extends outward from the main body. An extension locking mechanism within the main body locks the position of the second transport apparatus when the first holding member is moved from the first reference position and locks the position of the first transport apparatus when the second holding member is moved from the second reference position.

15 Claims, 8 Drawing Sheets

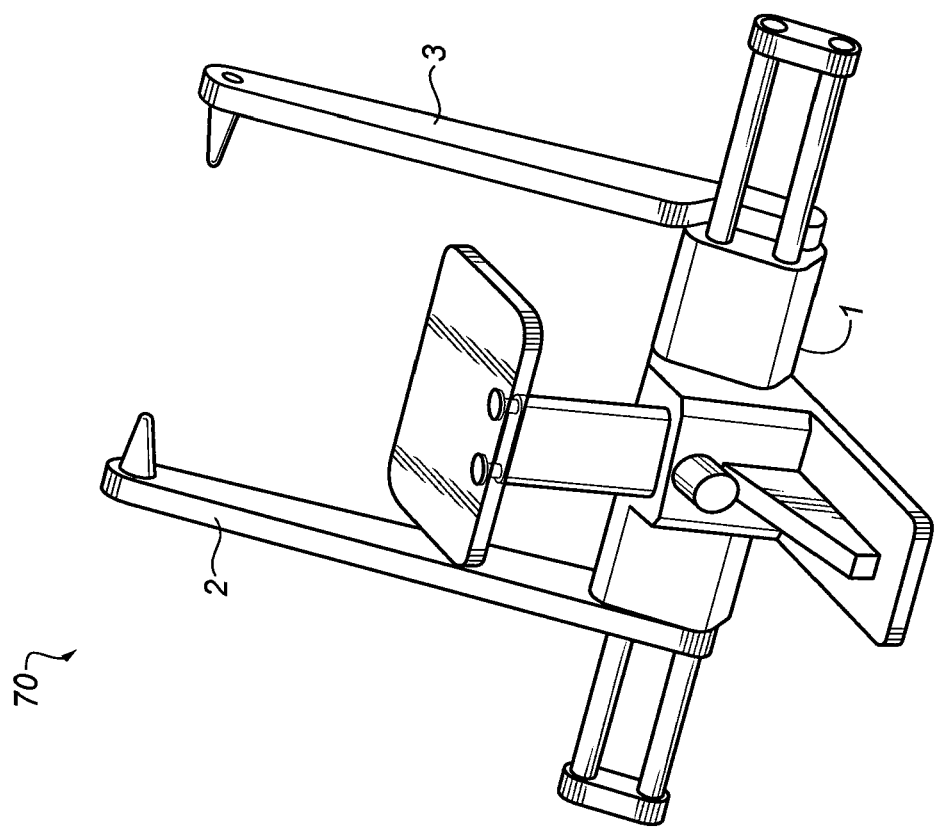

PATIENT HEAD SUPPORT APPARATUS FOR IMAGING

FIELD OF THE INVENTION

The present invention pertains to the X-ray imaging and more particularly to patient support apparatus for obtaining a volume image of structures within the human head, such as for ear, nose, and throat (ENT) images from Computerized Tomographic (CT) Imaging.

BACKGROUND OF THE INVENTION

A CT imaging apparatus operates by acquiring multiple 2D images with a rotating imaging ensemble or gantry that has an x-ray source and an imaging sensor rotating about a fixed axis relative to the patient. CT imaging allows the reconstruction of 3D or volume images of anatomical structures of the patient. Smaller, so-called "partial" CT imaging systems allow the use of a small size x-ray field focused on a local anatomical region of interest of the patient. In dental imaging, for example, a partial CT imaging system can be used for imaging two or three teeth. The advantage of such a technique is that it limits both the x-ray dose received by the patient and the size and cost of the sensor.

For CT imaging of the human head, the axis of rotation of the gantry structure that supports the x-ray source and the sensor has to be precisely positioned on a vertical line above the region of interest on the patient. This requires that the patient be precisely positioned and constrained from movement during the imaging sequence. In dental imaging, the patient is typically positioned using support devices such as a chin rest, a forehead support, a temple support and especially a bite to position the patient's fore-teeth. The axis of rotation of the gantry moves to a preset position so that the axis corresponds to a vertical line extending above the bite. The fore-teeth then serve as the reference point. If the dentist needs to capture a CT image of a molar, for example, the axis of rotation is translated in a (xy) horizontal plane to a preset position so that it extends along a vertical line through the molar. In some embodiments, the patient is rigidly fixed in position, such as with a strap surrounding the patient's head and affixed to both edges of a forehead support.

Requirements for patient support for ear, nose, and throat (ENT) partial CT imaging differ from those for dental imaging in a number of ways. For example, for imaging temporal bones, there is no need for a bite that constrains the foreteeth. Indeed, the fore-teeth cannot be used as reference point for ENT imaging as they are too distant from the ears and temporal bones. Consequently, the patient's ears serve as useful reference points for ENT imaging.

Various apparatus have been devised for stabilizing patient position for ENT imaging, including devices that employ temporal holding members that constrain the patient's ears. U.S. Pat. No. 3,737,660 entitled "Apparatus for Taking Tomograms of Parabolically Curved Objects" to Ando et al. describes a head stabilizing device with adjustable ear rods for centering the patient's head relative to a rotational axis. U.S. Pat. No. 5,642,392 entitled "Medical Radiographic Apparatus and Patient's Head Fixing Device" to Nakano et al. describes a patient frame that is intended to fix the angle and position of the head relative to a central axis for imaging.

While these solutions may provide some measure of support for the head of the patient, they require symmetric positioning of the head of the patient and centering between ear rods, and do not provide reference positions.

There is a need for patient support apparatus for obtaining a volume image of structures within the human head, wherein the apparatus provides reference positioning for the patient relative to the imaging system.

SUMMARY OF THE INVENTION

An object of the present invention is to advance the art of ENT imaging using a volume imaging apparatus.

Another object of the present invention is to provide volume ENT imaging with a variable axis of rotation.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a support apparatus for positioning a patient's head in an imaging apparatus, the support apparatus comprising: a main body that has opposing first and second sides and supports first and second holding members for positioning against the patient's head, wherein the first holding member has a first reference position along the first side of the main body and is coupled to a first transport apparatus that extends outward from the main body, wherein the second holding member has a second reference position along the second side of the main body and is coupled to a second transport apparatus that extends outward from the main body; and an extension locking mechanism within the main body that locks the position of the second transport apparatus when the first holding member is moved from the first reference position and that locks the position of the first transport apparatus when the second holding member is moved from the second reference position.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2A is a perspective view that shows an assembled head support apparatus according to an embodiment of the present invention.

DETAILED DESCRIPTION OF THE INVENTION

Figure 1A:
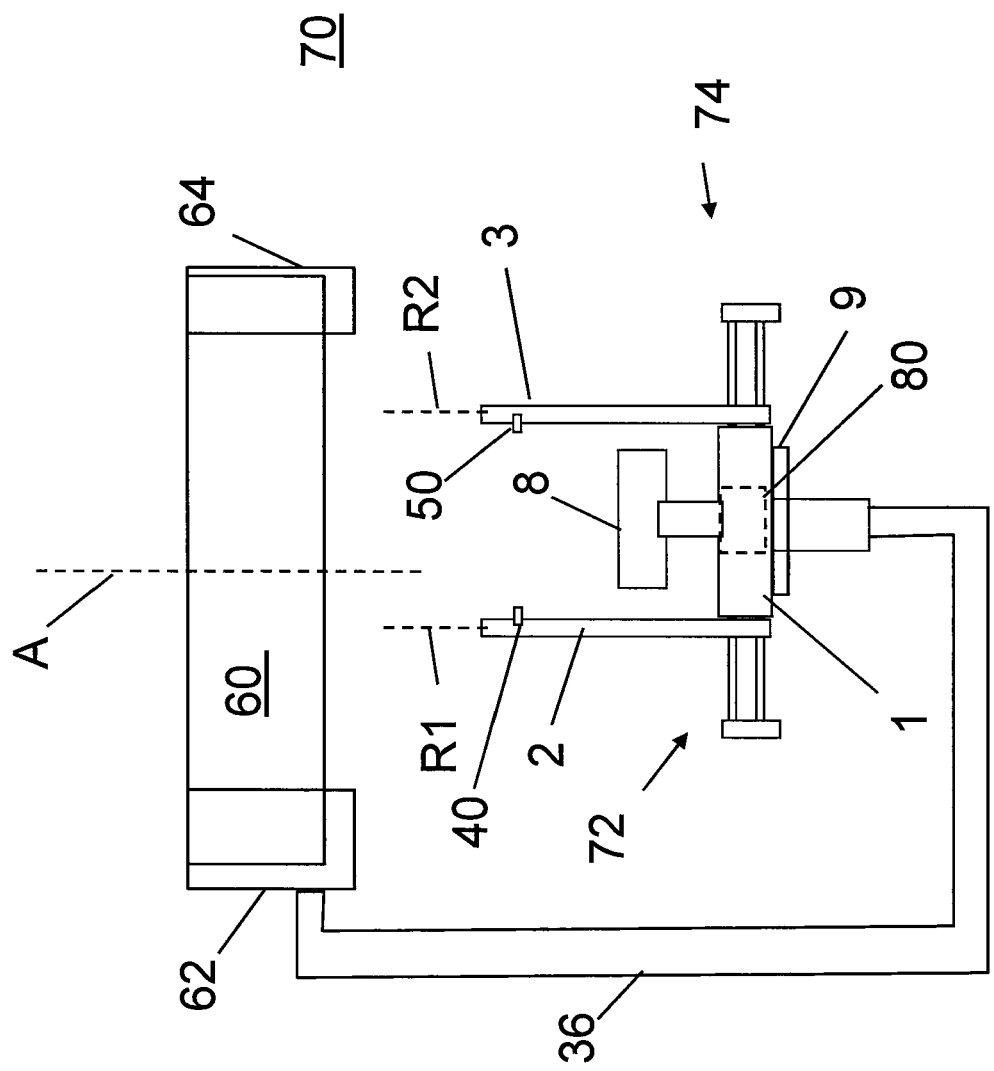
FIG. 1A shows a front view of components of a patient support for ENT and other imaging of structures in the head, with the components at rest position.

The following is a detailed description of the preferred embodiments of the invention, reference being made to the drawings in which the same reference numerals identify the same elements of structure in each of the several figures. It should be noted that these figures are provided to illustrate overall functions and relationships according to embodiments of the present invention and are not provided with intent to represent actual size or scale.

In the context of the present disclosure, the term "volume image" is synonymous with the terms "3-dimensional image" or "3-D image". Embodiments of the present invention, although developed primarily for the use in CT volume imaging can also be used for other types of volume imaging. To obtain a volume image, multiple images are taken and different angles relative to the imaged patient or other subject.

Where they are used, the terms "first", "second", "third", and so on, do not necessarily denote any ordinal or priority relation, but are simply used to more clearly distinguish one element from another.

The schematic block diagram of FIG. 1A shows features of a head support apparatus 70 at a rest position according to an embodiment of the present invention. Head support apparatus 70 mounts on a support structure 36 and has a main body 1, a base 9, and an optional chin rest 8. There are two temporal holding members 2 and 3 for positioning against the patient's head, each coupled to a transport apparatus, 72 and 74 respectively. Each holding member 2 and 3 has a respective reference position, shown as R1 and R2, respectively. Components of transport apparatus 72 and 74 include one or more shafts or other elements that extend outward, one from each side of main body 1. Ear rods 40 and 50 are provided for seating within outer portions of the patients' ear cavity. In the rest position shown in FIG. 1A, the distance between both ear rods 40 and 50 at the rest position is significantly smaller than the size of a patient's head. A rotatable gantry 60, also mounted on support structure 36, provides an x-ray source 62 and a sensor 64 for detecting x-rays and forming an image. Supporting structure 36 is representative in FIG. 1A and can take any number of forms for a standing or seated patient. Not shown are other conventional support components of the x-ray imaging apparatus, such as rotation mechanism for gantry 60 rotation, for example. A mouthpiece or bite structure could also be provided to help in further stabilizing the patient's head or in adjusting the head angle. As described in more detail subsequently, the position of axis of rotation A could vary, depending on whether reference position R1 or reference position R2 is fixed.

Figure 1B:
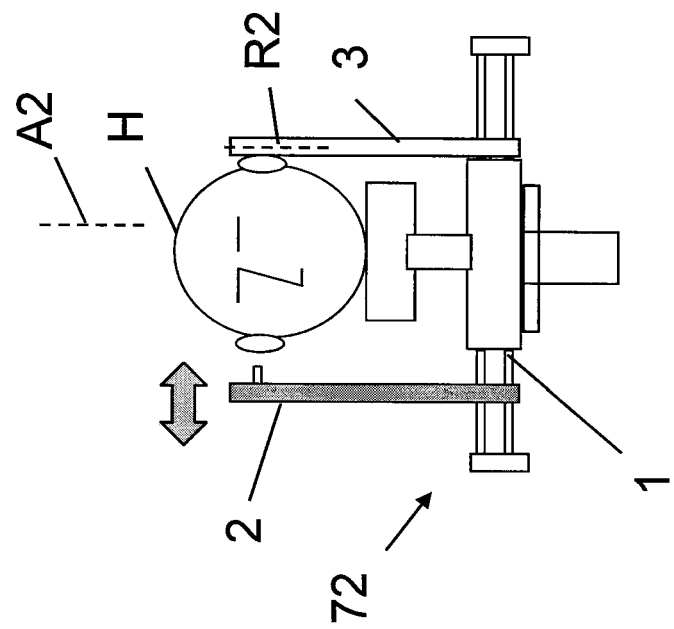
FIG. 1B shows a front view of components of a patient support for ENT and other imaging of structures in the head, with one holding member in motion.
Figure 1C:
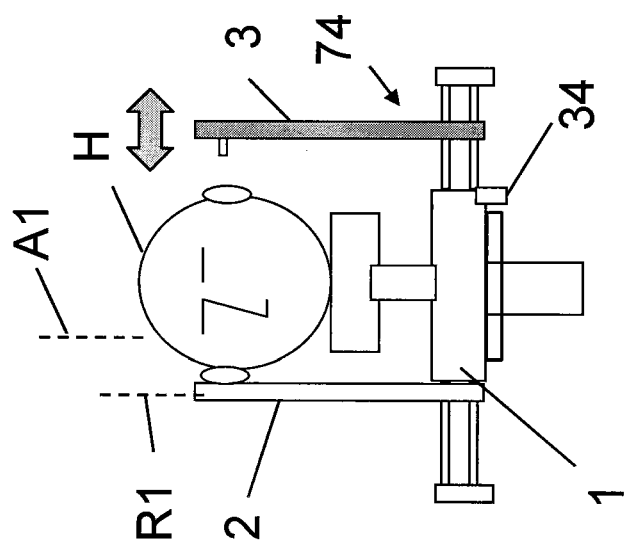
FIG. 1C shows a front view of components of a patient support for ENT and other imaging of structures in the head, with an alternate holding member in motion.

An extension locking mechanism 80, described in more detail subsequently, constrains movement of either of temporal holding members 2 and 3 at a time. As shown in FIG. 1B, when holding member 3 is moved outward from main body 1, holding member 2 is locked in its reference position R1. Similarly, as shown in FIG. 10, when holding member 2 is moved outward from main body 1, holding member 3 is locked in its reference position R2. In this way, only one of holding members 2 or 3 can be moved outward at one time. At any one time, either holding member 2 is at reference position R1 or holding member 3 is at reference position R2. This allows alternative references for supporting patient head H in position relative to an axis of rotation A1 or A2 for gantry rotation of the x-ray source and sensor during imaging. In one embodiment of the present invention, the axis of rotation can be set to either of two positions, shown as A1 and A2 in FIGS. 1B and 1C, allowing repositioning of the imaging gantry for imaging structures of the left or right ear when rotating along different axes, for example. Adjustment to position for axis A1 or A2 can be a mechanical adjustment made by an operator or may be automatically performed by control logic that operates the volume imaging apparatus. An optional sensor 34, as shown in FIG. 1B, enables control logic for the volume imaging apparatus to determine whether or not holding member 2 or 3 has been adjusted, so that proper axis selection can be enabled.

Figure 2B:
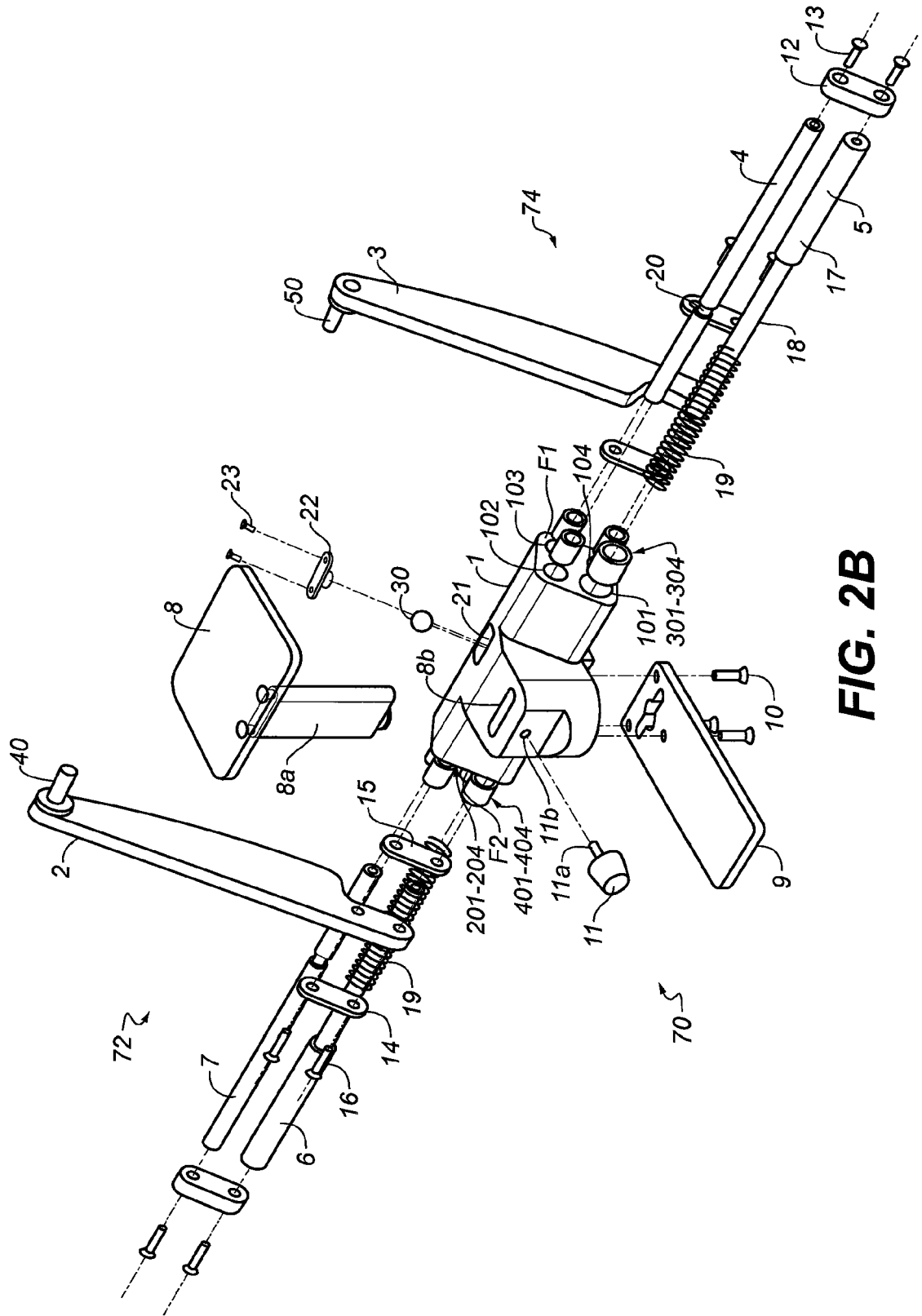
FIG. 2B is a perspective view that shows components of a head support apparatus according to an embodiment of the present invention.

The perspective view of FIG. 2A shows a head support apparatus 70 in an embodiment of the present invention. The perspective view of FIG. 2B shows components of head support apparatus 70 in detail. On one side of main body 1, holding member 2 is coupled to transport apparatus 72 along a pair of lateral shafts 6 and 7 that extend through main body 1. On the opposite side of main body 1, holding member 3 is coupled to transport apparatus 74 along a pair of lateral shafts 4 and 5 that extend through main body 1. Holding members 2 and 3 support corresponding ear rods 40 and 50 respectively. In the embodiment shown, base 9 is fastened to the main body 1 with three screws 10. The base 9 is coupled to the frame of an extra oral imaging device, for example along a horizontal arm (not represented) that is vertically adjustable to adjust the patient height. The optional chin support 8 comprises a vertical plate 8a screwed on its bottom face. The plate 8a can slide freely in a groove 8b of the main body 1 to adjust the vertical position of the chin relative to the main body and, as will be further described subsequently, relative to the ears of the patient. An adjustment control 11, such as an adjustment knob is provided, comprising a threaded shaft 11a cooperating with a threaded hole 11b that extends through the main body 1 from an outside face of the main body to the groove 8b. By turning control 11, the treaded shaft block the plate 8a of the chin rest 8 at the appropriate vertical position. It should be emphasized that chin support 8 is optional. Other types of supporting structures can be provided for stabilizing the position and angle of the chin or teeth, if such stabilization is needed.

Two screws 13 fasten a stopper 12 to one face at the extremity of both transport shafts 4 and 5. At the other end of the shafts, an extremity of the temporal holding member 2 is surrounded by two holders 14 and 15, these three pieces being affixed at the face of the other extremity of shafts 4 and 5 by two screws 16 or other fasteners. The shaft 5 comprises a larger diameter part 17 and a smaller diameter part 18. A spring 19 surrounds the smaller diameter part 18 and abuts against the face of the larger diameter part 17. The shaft 4 comprises a groove 20. In the present embodiment, the diameter of the shaft 4 is equal to the smaller diameter of the shaft 5, but this is not a necessity.

Main body 1 can be formed from metal or other suitable material that is capable of bearing weight and supporting the adjustable and stationary hardware shown. There are four channels extending through main body 1 from its right face F1 to its left face F2 on the opposite side. On right face F1 of main body 1 are four holes 101-104, the front bottom hole 101 as seen in the view of FIG. 2B being larger than the three others in the embodiment shown. On left face F2 are four holes 201-204. The rear bottom hole 204 is larger than the three other holes. Pairs of holes 101 and 201, 102 and 202, 103 and 203, 104 and 204 are each linked to each other by a parallel channel traversing the main body 1 from face F1 to face F2. Shaft 5 of transport apparatus 74 has a travel path that extends through main body 1 from larger diameter hole 101 at face F1 to the bottom front hole of smaller diameter 201 at opposing face F2. Shaft 4 has a travel path that extends within the main body 1 from hole 102 to front upper hole 202. Shaft 6 has similar structure to shaft 5, comprising two sections of different diameters. The smaller diameter section of shaft 6 has a surrounding spring 19; shaft 6 extends into the main body 1 through the rear bottom hole 204 of larger diameter and exits main body 1 through the rear bottom hole 104. Shaft 7 has similar structure to shaft 4; shaft 7 has one single section and one groove, extending into main body 1 through rear top hole 203 and exiting main body 1 through rear top hole 103. Holding member 3 is coupled to shafts 6 and 7 of transport apparatus 74 using an arrangement of plates and fasteners, as shown in FIG. 2B. Each of the four shafts 4, 5, 6, and 7 has corresponding sleeves 301-304 and 401-404, installed along faces F1 and F2; these sleeves help to diminish friction as the shafts slide within their respective channels inside main body 1.

Still referring to FIG. 2B, an extension locking mechanism 80 has a spherical element, ball 30, of controlled diameter located in a vertical channel 21 extending from the top face of the main body 1. A stopper 22, affixed to the top surface of main body 1 by screws 23 or other fasteners, helps to retain ball 30 in position within main body 1.

Figure 3:
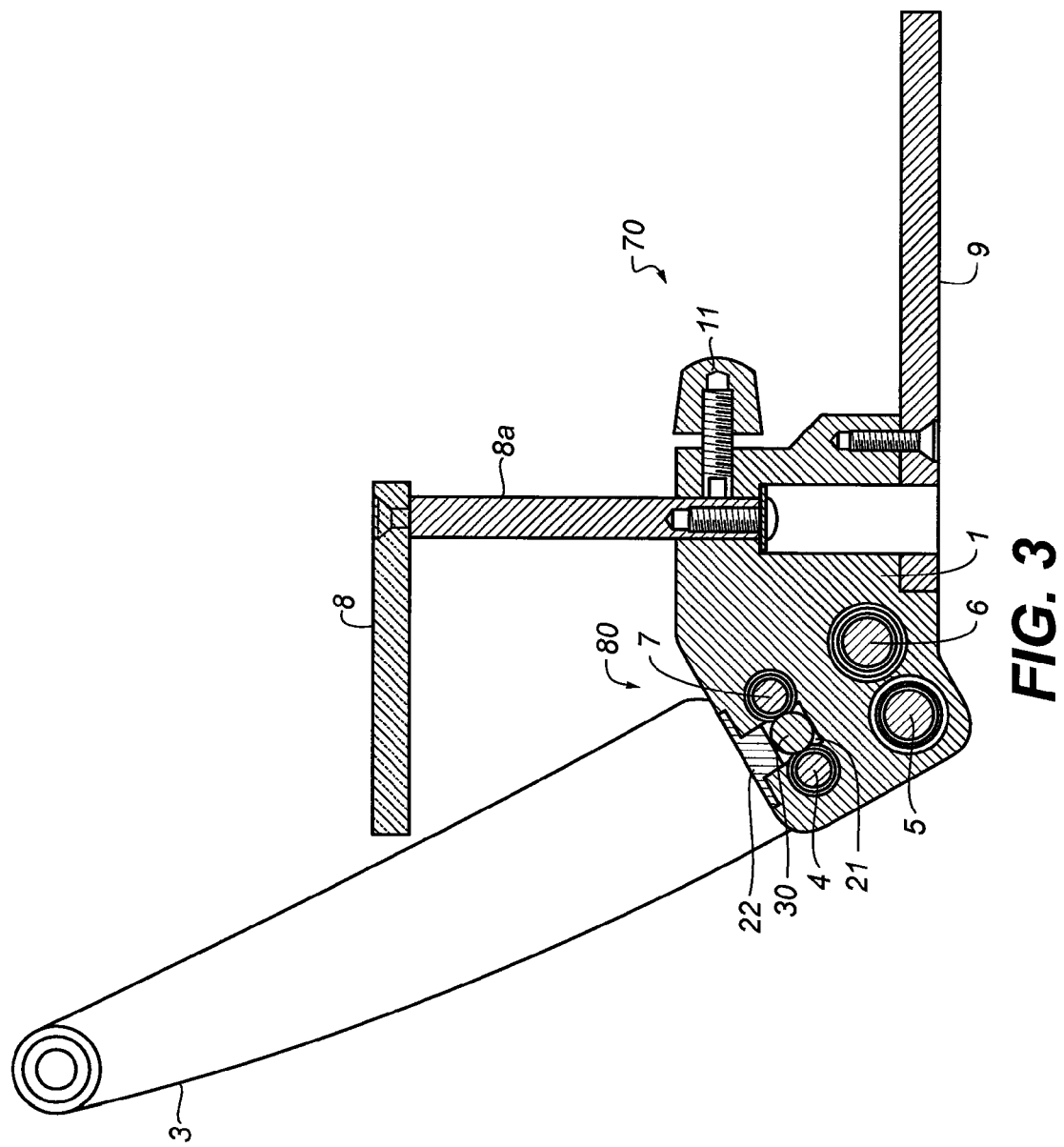
FIG. 3 is a side view of the head support apparatus showing shaft positions.

FIG. 3 is a partial cross-section side view taken through main body 1 and shows components of extension locking mechanism 80 in more detail. When inserted in channel 21, ball 30 drops so that it seats along the bottom of the channel and in contact against shafts 4 and 7. This view has the support in the "rest position" of FIG. 1A (described below in further detail). In rest position, holding members 2 and 3 are in their respective reference positions, each contacting its corresponding face F1 and F2 of main body 1. Respective grooves 20 in shafts 4 and 7 are centered, aligned with channel 21 of extension locking mechanism 80. Ball 30 lies within the grooves 20 of both shafts 4 and 7 when both are in reference position.

Figure 4:
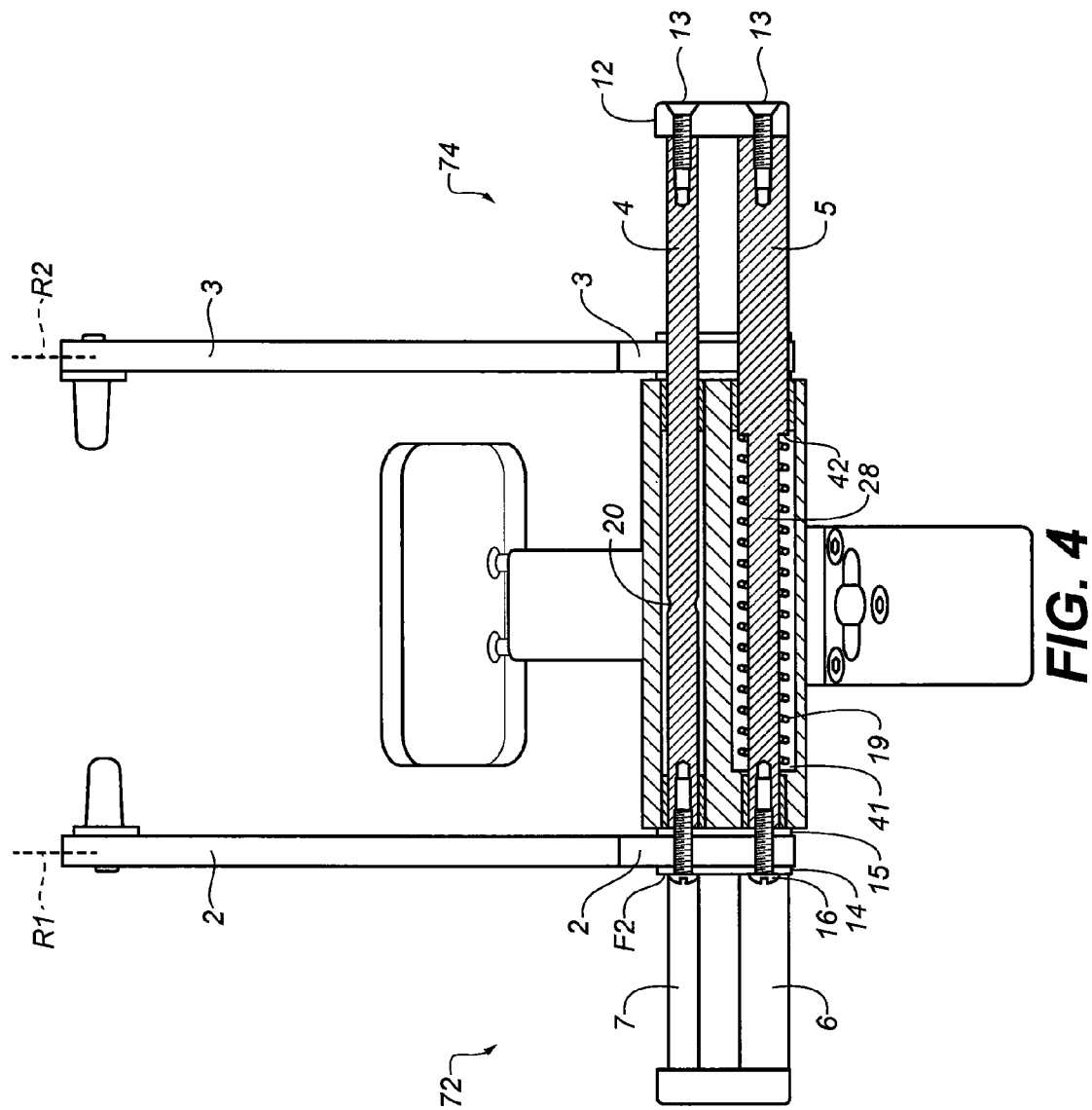
FIG. 4 is a cross-section view of the head support apparatus showing how one pair of shafts extends within the main body, at rest position.

FIG. 4 is a front view cross-section that shows shafts 4 and 5 extended within main body 1. As with FIG. 3, FIG. 4 also represents the rest position of the patient support apparatus 70, in which holding members 2 and 3 are both in their respective reference positions R1 and R2 as was noted previously with respect to FIG. 1A. Shaft 5 extends along a channel 28 that has a shoulder 41. Spring 19 about shaft 5 presses against shoulder 41 and applies a force directed to the right on a face 42 of the shaft 5, the force tending to restore the holding member 2 to its reference position. Consequently, with holding member 2 coupled to shaft 5, light pressure from this spring force causes contact between holder 15 and the left face F2 of main body 1. Shaft 4 is similarly coupled to holding member 2. When holding members 2 and 3 are the rest position, groove 20 located on the mid-plan of the main body 1.

For the same reason, in the rest position, temporal holding member 3 abuts right face F1 of main body 1 and the groove of shaft 7 lies within main body 1 and faces the groove of shaft 4. Ball 30 in its channel 21 also lies in within main body 1. In the rest position, ball 30 is seated in both grooves 20 of shafts 4 and 7. Either transport apparatus 72 or 74 is movable from the rest position, with ball 30 in both grooves 20. Only one of the transport apparatus 72 or 74 can be moved from this position at a time, however.

Figure 5:
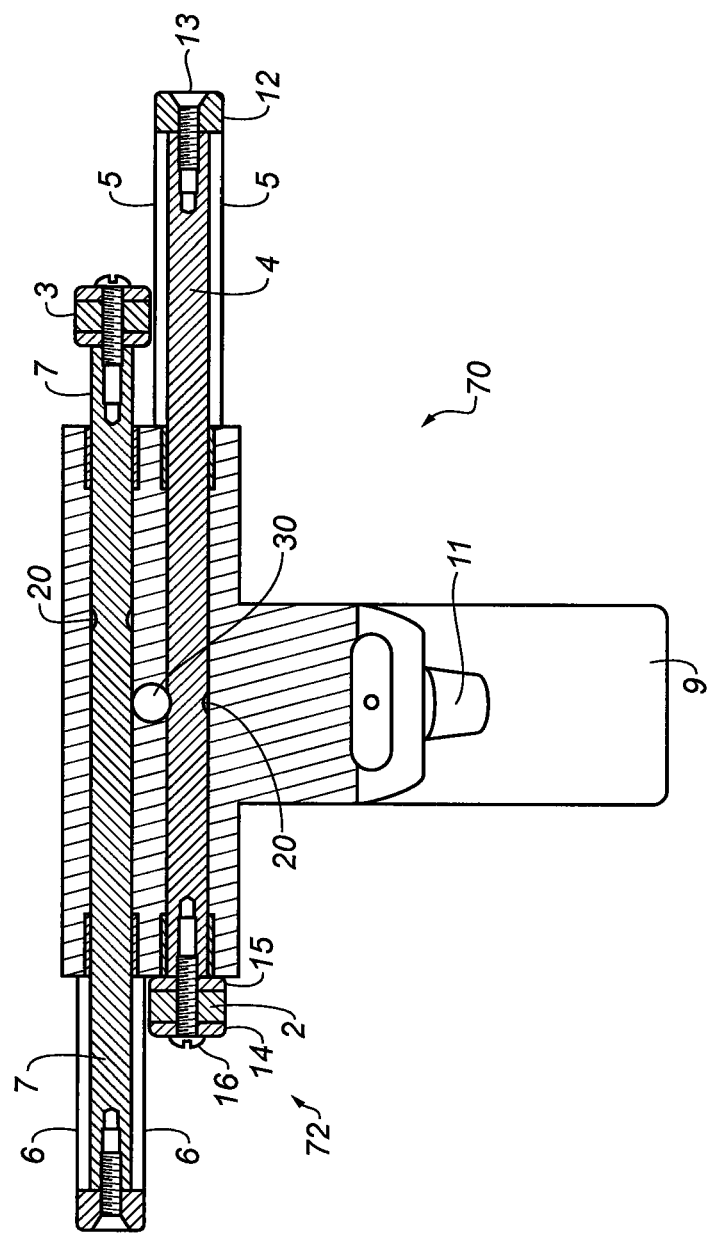
FIG. 5 is a cross-section view of the head support apparatus showing how one pair of shafts extends within the main body, with one transport apparatus movable.

FIG. 5 is a cross-section view of head support apparatus 70 in the plane defined by the axis of both shafts 4 and 7, showing how one pair of shafts extends within main body 1, with transport apparatus 74 (shafts 6 and 7) movable and transport apparatus 72 (shafts 4 and 5) locked in place, corresponding to the schematic view of FIG. 1B.

When an ENT CT image is desired, such as an image of the temporal bone of the right or left ear, the practitioner seats the patient and, with temporal holding member 2 in position against main body 1, adjusts temporal holding member 3 for the patient's head, exerting a lateral force to counterbalance the force created by the return spring and to remove holding member 3 from its rest position. With this motion, transport apparatus 72, coupled to holding member 3 can be laterally displaced. Ball 30 is forced out from groove 20 of shaft 7, but remains seated in groove 20 of corresponding shaft 4 for transport apparatus 74. Shaft 7 slides along ball 30 with a type of bearing contact, sliding on a single contact point; shaft 4 is locked in place by ball 30.

With temporal holding member 3 out of its rest position, the other temporal holding member 2, coupled to shaft 4 of transport apparatus 74, cannot move from its rest position because ball 30 is trapped in channel 21 (FIG. 2B) between groove 20 of shaft 4 and the lateral face of shaft 7. The diameter of ball 30 is small enough so that ball 30 can be located in groove 20 of one shaft while out of groove 20 of the other shaft, facing this latter shaft and providing single-point bearing contact as the shaft moves. Ball 30 is large enough so that it cannot be unseated from both grooves 20 while facing both shafts. With ball 30 trapped, shaft 4 and its corresponding temporal holding member 2 are in a fixed position relative to main body 1 and, consequently, also in a fixed position relative to the gantry supporting the x-ray source and sensor.

When the patient positioned for a right ear CT image, the practitioner displaces temporal holding member 3 on the left (relative to the patient), positions the chin on chin rest 8, positions the patient's head so that ear rod 40 on temporal holding member 2 slightly penetrates his right ear cavity. The practitioner then releases the force exerted on temporal holding member 3. The force of return spring 19 surrounding shaft 6 gently moves holding member 3 back toward the rest position. The patient positions his head so that ear rod 50 on holding member 3 slightly penetrates the left ear cavity.

When properly positioned using head support apparatus 70, the patient can be held on three non planar points: at the chin and at two ears, so that the patient's head is stabilized and does not move during imaging. The ear rod 40, and consequently the right ear of the patient, are in a well-defined position relative to the gantry and its related imaging components. It should be noted that the patient's head position can be different based on whether holding member 2 or holding member 3 is adjusted. In addition, chin rest 8 is optional, so that angular movement of the patient's head may be constrained by other means if needed.

Figure 6:
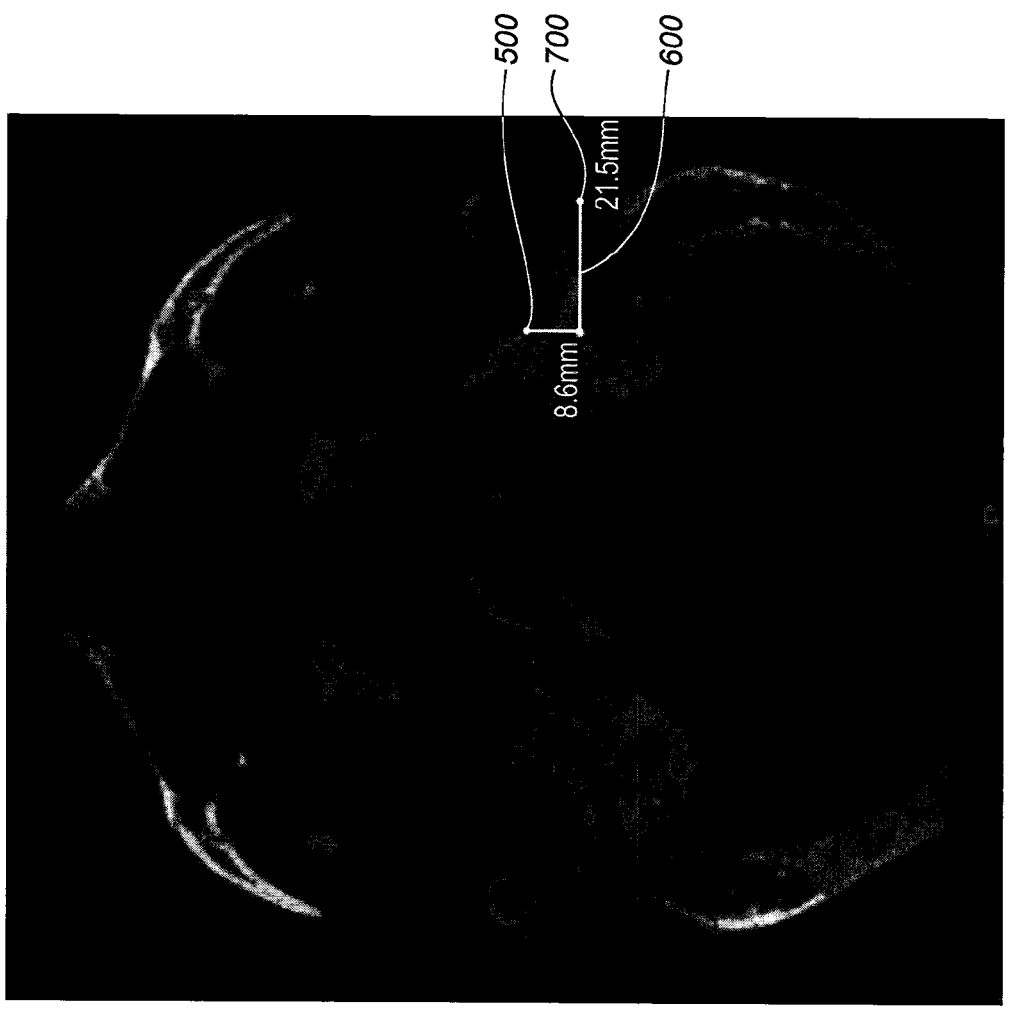
FIG. 6 is an image of the head obtained in 3D using a volume imaging apparatus with adjustable holding members.

FIG. 6 is a horizontal cross view (viewed from above) of the skull of a patient. The temporal bone 500 to be imaged is located at a known distance from the location 700 of the extremity of the ear rod in the right ear canal 600, this distance only slightly depending of the patient. This defines a preset position in a horizontal plane (xy) of the vertical swivel axis of the gantry about which the x-ray source and sensor rotate during the CT capture. The software operating logic of the extra-oral imaging system can then direct the swivel axis to either of two preset positions: one for each ear CT capture.

The invention has been described in detail with particular reference to a presently preferred embodiment, but it will be understood that variations and modifications can be effected within the spirit and scope of the invention. For example, a bite or other element could optionally be provided in order to provide improved head stabilization and angular orientation. Alternate techniques could be used to provide the extension locking mechanism that allows movement of only one of the two transport apparatus. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A support apparatus for positioning a patient's head in an imaging apparatus, comprising:
 a main body having opposing first and second sides and to support first and second holding members for positioning against the patient's head,
 wherein the first holding member has a first reference position and is coupled to a first transport apparatus, where the first transport apparatus is coupled to the first side of the main body and configured to move the first holding member relative to the second holding member, and
 wherein the second holding member has a second reference position and is coupled to a second transport apparatus, where the second transport apparatus is coupled to the second side of the main body and configured to move the second holding member relative to the first holding member; and
 an extension locking mechanism that locks the position of the second transport apparatus when the first holding member is moved from the first reference position and that locks the position of the first transport apparatus when the second holding member is moved from the second reference position, where the first reference position and the second reference position are relative to the imaging apparatus.

2. The support apparatus of claim 1 wherein the main body further comprises a chin rest.

3. The support apparatus of claim 1 wherein a portion of the first and second holding members seats against the patient's right and left ear cavities.

4. The support apparatus of claim 1 wherein the imaging apparatus comprises a gantry that rotates about an axis and comprises:
 an x-ray source; and
 a sensor for detecting x-rays having passed though an object.

5. The support apparatus of claim 1 wherein the first transport apparatus comprises one or more shafts that pass through the main body.

6. The support apparatus of claim 5 wherein the extension locking mechanism comprises a spherical element that seats within a groove in at least one of the one or more shafts.

7. The support apparatus of claim 1 wherein the first transport apparatus further comprises a return spring that applies a force to restore the first holding member to the first reference position.

8. The support apparatus of claim 4 wherein the axis of the gantry has two or more positions according to whether or not the first or the second holding member is in its respective reference position.

9. The support apparatus of claim 1 wherein the first transport apparatus comprises a sensor for sensing movement of the first holding member.

10. A method for obtaining a volume image of a patient's head using an imaging apparatus, comprising:
 providing a main body having opposing first and second sides that respectively support first and second holding members for positioning against the patient's head,
 where a first transport apparatus is coupled to the first side of the main body and coupled to the first holding member, where the first transport apparatus is configured to move the first holding member at least laterally relative to the second holding member,
 where a second transport apparatus is coupled to the second side of the main body and coupled to the second holding member, where the second transport apparatus is configured to move the second holding member at least laterally relative to the first holding member;
 allowing adjustment of the first holding member away from a first reference position while, at the same time, constraining adjustment of the second holding member at a second reference position;
 adjusting the position of an axis of rotation according to the second reference position of the second holding member; and
 rotating a gantry about the adjusted axis of rotation to obtain the volume image of the patient's head, where the first reference position and the second reference position are relative to the imaging apparatus.

11. The method of claim 10 wherein adjusting the position of the axis of rotation is performed by control logic of the imaging apparatus.

12. The support apparatus of claim 1, where the first transport apparatus is directly connected between the main body and the first holding member, where the second transport apparatus is directly connected between the main body and the second holding member.

13. The support apparatus of claim 1, where the extension locking mechanism locks the position of the second transport apparatus in the second reference position when the first holding member is moved from the first reference position, and the extension locking mechanism locks the position of the first transport apparatus in the first reference position when the second holding member is moved from the second reference position.

14. The support apparatus of claim 1, where the first transport apparatus is configured to move the first holding member at least laterally relative to the second holding member, and where the second transport apparatus is configured to move the second holding member at least laterally relative to the first holding member.

15. The support apparatus of claim 1, where the extension locking mechanism is coupled to or within the main body.

* * * * *